(12) United States Patent
Helmfridsson et al.

(10) Patent No.: US 8,475,426 B2
(45) Date of Patent: Jul. 2, 2013

(54) MALE INCONTINENCE PROTECTOR

(75) Inventors: Bror-Inge Helmfridsson, Partille (SE); Ken Olsson, Västra Frölunda (SE)

(73) Assignee: SCA Hygiene Products AB, Göteborg (SE)

( * ) Notice: Subject to any disclaimer, the term of this patent is extended or adjusted under 35 U.S.C. 154(b) by 624 days.

(21) Appl. No.: 11/980,540

(22) Filed: Oct. 31, 2007

(65) Prior Publication Data

US 2008/0082072 A1    Apr. 3, 2008

Related U.S. Application Data

(63) Continuation of application No. PCT/SE2005/000694, filed on May 16, 2005.

(51) Int. Cl.
*A61F 13/15* (2006.01)

(52) U.S. Cl.
USPC ............ 604/385.19; 604/385.01; 604/385.27; 604/385.28; 604/385.24; 604/385.25; 604/385.26

(58) Field of Classification Search
USPC ........................... 604/385.19, 385.27, 385.28
See application file for complete search history.

(56) References Cited

U.S. PATENT DOCUMENTS

| | | | | |
|---|---|---|---|---|
| 5,558,659 | A | * | 9/1996 | Sherrod et al. ............ 604/385.26 |
| 6,371,950 | B1 | * | 4/2002 | Roslansky et al. ....... 604/385.19 |
| 2006/0282055 | A1 | | 12/2006 | Shiomi et al. |

FOREIGN PATENT DOCUMENTS

| | | |
|---|---|---|
| CN | 1142755 | 2/1997 |
| GB | 2 296 440 A | 7/1996 |
| JP | 60-69114 U | 5/1985 |
| JP | 07-124190 A | 5/1995 |
| JP | 2002-360622 A | 12/2002 |
| JP | 2004-121386 A | 4/2004 |
| SE | 449 172 B | 7/1987 |
| SE | 450 811 B | 8/1987 |
| SE | 500 793 C2 | 9/1994 |
| SE | 508 240 C2 | 9/1998 |
| WO | WO 86/06620 A1 | 11/1986 |
| WO | WO 91/07155 A1 | 5/1991 |
| WO | WO 2004/019850 A1 | 3/2004 |
| WO | WO 2004/087027 | 10/2004 |

OTHER PUBLICATIONS

PCT/ISA/210 dated Oct. 24, 2005.
An English Translation of the Notification of the First Office Action issued in the corresponding Chinese Patent Application No. 200580049805.4 dated Mar. 26, 2010.
An English Translation of the Examination Report issued in the corresponding Japanese Patent Application No. 2008-512242 dated Aug. 24, 2010.
Japanese Notice of Reasons for Rejection dated May 24, 2011 issued in the corresponding Japanese Patent Application No. 2008-512242, and English-language translation.

* cited by examiner

*Primary Examiner* — Tatyana Zalukaeva
*Assistant Examiner* — Ilya Treyger
(74) *Attorney, Agent, or Firm* — Buchanan Ingersoll & Rooney PC

(57) ABSTRACT

An incontinence protector for males intended for disposable use, including a fastening pocket for fastening the genitalia during use.

20 Claims, 2 Drawing Sheets

MALE INCONTINENCE PROTECTOR

TECHNICAL FIELD

The present invention relates to a disposable incontinence protector for males. The incontinence protector has a front transverse edge intended to be facing forwards during use and a rear transverse edge intended to be facing rearwards during use, and two longitudinal edges. The incontinence protector further comprises an upper liquid-permeable casing layer, a lower backing layer and an absorption body disposed between the liquid-permeable casing layer and the backing layer.

BACKGROUND

What is often referred to as mild incontinence and entails leakage of minor quantities of urine is not considered a mild complaint for the person afflicted. Mild incontinence is a hidden handicap, from which many people suffer. A large group of mildly incontinent men is constituted by men with prostate disorders. Many men, following a prostate operation, acquire problems with drip incontinence, which has hitherto led to mental anguish for many, since there have been no suitable incontinence protectors available.

Previously used incontinence protectors for men suffering from so-called mild incontinence are characterized in that they are often constructed in the same way as incontinence protectors intended for women suffering from mild forms of incontinence. Often, even the same types of incontinence protectors are used for both men and women. This is due to the fact that mild incontinence is more common amongst women than amongst men, with the result that incontinence protectors for women are better known and there are more variants to choose from. The incontinence protectors are specially tailored to the female anatomy and are therefore by no means especially suitable for the male anatomy.

It is also common for mildly incontinent men to use incontinence protectors intended for more severe forms of incontinence. These incontinence protectors are intended to work for both urinary incontinence and faecal incontinence and are both large and cumbersome to wear for men who are merely urine-incontinent. The use of cumbersome incontinence pads of this kind implies a major restriction in terms of men's desire to engage socially within society. These incontinence protectors are, moreover, uncomfortable to wear and extremely indiscreet beneath normal clothing.

Special incontinence protectors intended for men with mild incontinence have previously been known, but effective solutions for such incontinence protectors continue largely to be lacking.

A commonly used type of specially designed incontinence protector for urine-incontinent men comprises a substantially conical container intended to enclose the penis (and sometimes also the scrotum) of the user. The conical container usually consists of absorption material, a liquid-permeable casing material next to the genitalia of the user and a liquid-impermeable barrier layer on the outside, facing out to the environment.

The principal drawback with incontinence protectors of this type is that they are far too hot and tight and hence uncomfortable to wear for the user. An additional drawback is that the protectors, as a result of their design, are rigid and uncomfortable, with a tendency to inflict chafing or some other discomfort upon the user.

The fastening of the protectors is achieved by the conical container being clasped around the penis of the user. For certain incontinence protectors, the fastening can also be achieved by the outer side of the conical container comprising an adhesive surface, a hook-and-loop surface or the like, which is intended to be fastened to the underclothes of the user. A combination of fastening to the body and to the underclothes of the user can also be found.

One example of an incontinence protector intended for male urine-incontinent users is described in Swedish patent SE 449172. The document describes an incontinence protector for males suffering from milder forms of urinary incontinence. The protector is configured as an absorbent collecting bag intended to enclose the genitalia of the user. The opening in the collecting bag comprises a cutout in that part of the bag which is intended to be facing towards the user during use. When the protector is in use, the cutout should be positioned beneath the scrotum of the user so that the scrotum is placed inside the collecting bag together with the penis. The protector is fastened to the underpants of the user by means of an adhesive surface on the outer side of the collecting bag. A certain fastening effect is also obtained by the fact that the incontinence protector grips gently around the penis and scrotum during use. The protector comprises a plastic outer side, a liquid-permeable nonwoven layer next to the genitalia of the user, that is to say inside the collecting bag, and an absorbent structure between the plastic layer and the nonwoven layer.

A drawback with the incontinence protector described in SE 449172 is that it is hot and uncomfortable to wear as a result of the genitalia of the user being fully enclosed by all the material layers of the incontinence protector.

Another drawback is that the incontinence protector is fastened to the underclothes of the user, which implies a risk of the incontinence protector ending up remote from the penis of the user. Elderly males, the most commonly occurring category of men with incontinence problems, often tend to choose underclothes which fit loosely around the body, so that the problem of the incontinence protector ending up remote from the body is relatively prevalent. Leakage is virtually inevitable once the incontinence protector has distanced itself from the penis of the user.

Another type of incontinence protector for men is known from Swedish patent SE 450 811. The protector consists of an upper screen-like part, which, when the protector is in use, lies snugly over the penis and scrotum, and a lower part, which, when the protector is in use, curves in beneath the penis and scrotum of the user without fully enclosing them. The protector has a downward-tapering and bowl-like shape. With such a protector, a tight enclosure of the genitalia of the user is therefore avoided, which is naturally an advantage from the comfort aspect.

The protector is held in place by means of double-sided adhesive tape, arranged on the side of the protector which, during use, is facing away from the user, the double-sided adhesive tape being arranged such that the fastening is made to the pants of the user or to special fixation pants in the crotch section.

The problem with such an incontinence protector is that it does not work at all well with underpants which fit loosely around the genitalia of the user, since there is no fastening to the user.

In another patent, SE 500793, an incontinence protector is described which also has a downward-tapering and bowl-like shape. The protector, which in the extended state, has the shape of a triangle, comprises a liquid-permeable surface layer arranged on the side of the protector which, during use, is facing towards the user, a liquid-impermeable surface layer on the opposite side and an absorption body arranged between the surface layers. Along the two substantially longitudinal edges of the protector, elastic members are arranged between the surface layers, whereby the protector acquires a curved bowl shape when the elastic members contract from their, in the production, stretched state.

The patent does not describe how the protector is fastened to the user or the pants of the user during use, but it can be assumed that the protector is intended for use together with relatively tight-fitting underpants, the protector being expected to be held in place by the underpants without any special fastening members or by means of some form of fastening member, such as, for example, pressure-sensitive glue or hook-and-loop fastenings, to the underpants of the user in the crotch section.

The same problems as for the incontinence protector described in patent SE 450 811, with respect to the fastening of the incontinence protector, are also present for this incontinence protector.

Swedish patent specification SE 508240 describes an incontinence protector for men which has an initially rectangular material piece comprising a liquid-permeable surface layer arranged on the side of the protector which, during use, is facing towards the user, a liquid-impermeable surface layer on the opposite side and an absorption body arranged between the surface layers. Both edges of the material piece which are intended to extend in the direction away from the crotch section of the user towards the abdomen of the user are Z-folded, a channel having been created between the Z-folded edges. The Z-folded shape has been locked in its position by sealing of the transverse edge which is intended to be positioned at the back on the user. In addition to its form-preserving function, the seal also constitutes a barrier for urine flowing back past the rear transverse section of the incontinence protector.

When the protector is in use, the Z-folded edge regions which have not been sealed are pulled apart, whereupon the seal along the rear transverse edge holds the protector together in its rear end section. The protector has in this case a downward-tapering and bowl-like shape. The protector is held in place by means of hook-and-loop material, arranged on the side of the protector which, during use, is facing away from the user, the hook-and-loop material being arranged such that the fastening is made to the underpants of the user in the crotch section.

For this incontinence protector also, the problem exists that the protector easily distances itself from the genitalia of the user, which can lead the protector to leak.

It is generally the case with incontinence protectors fastened to the underpants of the user that they adapt to the crotch position of the fixation pants during use. When fastened to pants or fixation pants with voluminous crotch sections, this means that the incontinence protector adopts a position a little bit away from the genitalia of the user, and that the incontinence protector tends to move relative to the genitalia of the user whenever he moves. An incontinence protector which does not lie snugly against the genitalia of the user during urination implies a substantially increased risk of leakage. There is also a comfort problem associated with incontinence protectors which can shift in a more or less uncontrolled manner relative to the body of the user during use.

Incontinence protectors which are clasped onto the penis of the user usually feel uncomfortable since they get far too hot when they are used. It is therefore quite common for elderly senile men, in particular, to attempt to remove the uncomfortable incontinence protector from the body.

There therefore remains a need for an improved fastening system for mild incontinence protectors intended for urine-incontinent men. The incontinence protector must be comfortable to use and offer effective fastening of the incontinence protector throughout the time in which the protector is worn. The fastening system must further be configured such that the incontinence protector is held in place against the genitalia of the user throughout the period of use, regardless of whether the user of the incontinence protector prefers underpants or fixation pants with voluminous or tightly fitting crotch section.

SUMMARY

A male incontinence protector of the type discussed in the introduction has been achieved, which male incontinence protector substantially eliminates the problems associated with previously known such protectors.

A male incontinence protector of the type discussed in the introduction is primarily distinguished by the fact that a substantially non-absorbent material layer is disposed on the side of the liquid-permeable casing layer which is orientated away from the absorption body, the periphery of the material layer being connected to at least one of the liquid-permeable casing layer or the backing layer along the rear transverse edge and along the two longitudinal edges. The material layer has a front transverse edge, the front transverse edge being free. A pocket is herein formed between the material layer and the liquid-permeable casing layer, the opening in the pocket being disposed at the front transverse edge of the material layer.

An incontinence protector is hereby obtained which is fastened directly to the genitalia of the user by the genitalia of the user being placed inside the pocket created between the material layer and the liquid-permeable casing layer of the incontinence protector. Owing to the fact that the material layer is thin and non-absorbent, the protector does not get hot and uncomfortable to wear. Furthermore, the fastening of the incontinence protector to the genitalia of the user is independent of the type of underclothes which is used, since the fastening is directly to the genitalia of the user.

According to one embodiment of the invention, the substantially non-absorbent material layer is constituted by a mesh.

The open mesh offers an especially airy and comfortable fastening when the incontinence protector is fastened by placement of the penis inside the pocket created between the liquid-permeable casing layer of the incontinence protector and the material layer constituted by the open mesh.

When the incontinence protector is fastened in an alternative manner, that is to say when the penis is placed outside the pocket, the open mesh constitutes minimal flow resistance for urine flowing into the incontinence protector.

According to another embodiment, the substantially non-absorbent material layer is constituted by a nonwoven.

According to one embodiment, the substantially non-absorbent material layer exhibits elastic properties, which improves the capacity of the pocket to enclose the penis when the incontinence protector is fastened with the penis inside the pocket.

According to one embodiment, the substantially non-absorbent material layer comprises elastic members.

The method of making the substantially non-absorbent material layer elastic by applying one or more elastic members to the material layer is a proven method for elastifying a material layer in an absorbent article.

According to one embodiment, the elastic members are constituted by elastic threads or elastic ribbons, the threads or ribbons extending substantially in the transverse direction of the incontinence protector.

Elastic properties of the substantially non-absorbent material layer in the transverse direction of the incontinence protector mean that the pocket, during use, encloses the penis very effectively.

According to one embodiment, the substantially non-absorbent material layer is constituted by an elastic nonwoven.

DESCRIPTION OF THE FIGURES

The embodiments of the invention will be described in greater detail below with reference to the figures shown in the appended drawings.

DESCRIPTION OF PREFERRED EMBODIMENTS

This disclosure relates to a mild incontinence protector for men.

Figure 1:
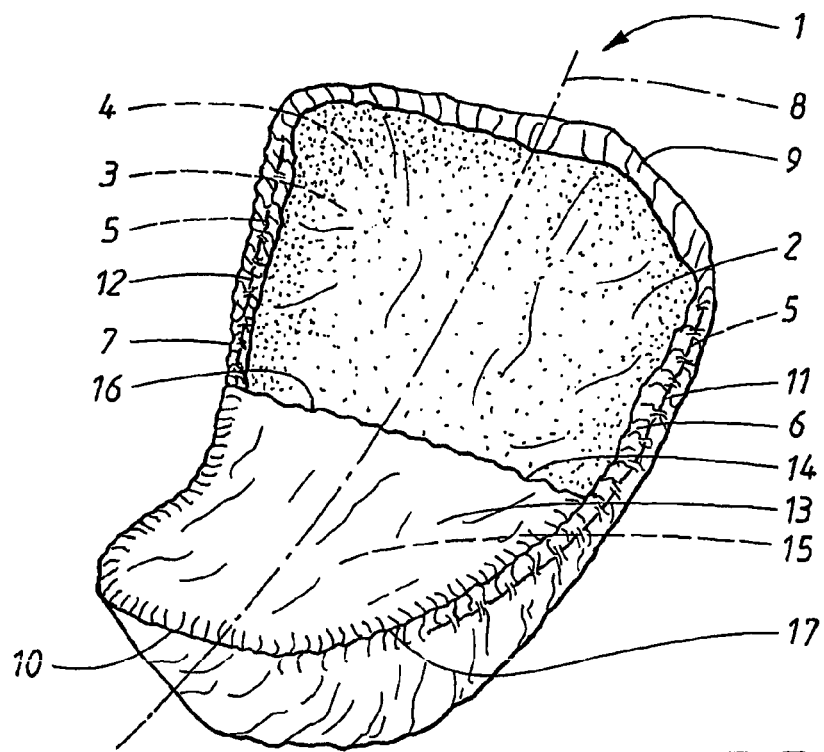
FIG. 1 shows a first embodiment of an incontinence protector according to the invention, viewed from the side which, during use, is intended to be facing towards the user.

The first embodiment shown in FIG. 1 relates to an incontinence protector 1 for mildly incontinent men. FIG. 1 shows the incontinence protector 1 viewed from the side which, during use, is intended to be facing towards the user in a usage-like curved configuration.

The incontinence protector 1 has a substantially isosceles triangular shape, the two longitudinal edges 6, 7 of equal length extending substantially in the same direction as the longitudinal line of symmetry 8 of the incontinence protector 1. A third edge constitutes the front transverse edge 9 of the incontinence protector 1 and extends transversely to the longitudinal line of symmetry 8 of the incontinence protector 1. The incontinence protector 1 further has a rear transverse edge 10, also extending transversely to the longitudinal line of symmetry 8 of the incontinence protector 1. The rear transverse edge 10 is disposed where the incontinence protector 1 is narrowest transversely to the line of symmetry 8. The rear transverse edge 10 is intended to be orientated rearwards during use of the incontinence protector 1, and the front transverse edge 9 is intended to be facing forwards towards the abdomen of the user.

The incontinence protector 1 comprises a liquid-permeable casing layer 2, disposed over the surface of the incontinence protector 1 which, during use, is intended to be facing towards the user, a backing layer 3, disposed over the surface of the incontinence protector 1 which, during use, is intended to be facing away from the user, and an absorption body 4, enclosed between the liquid-permeable casing layer 2 and the backing layer 3.

The liquid-permeable casing layer 2 of the incontinence protector 1 extends beyond the absorption body 4 along the whole of the circumference of the absorption body 4.

The liquid-permeable casing layer 2 can consist of any material which is suitable for the purpose. Examples of commonly found liquid-permeable casing materials are nonwoven materials, perforated plastic films, plastic or textile meshes, and liquid-permeable foam layers. Liquid-permeable casing materials which are constituted by continuous thin fibres extending substantially in the longitudinal or transverse direction of the product are also found. Laminates consisting of two or more of the abovementioned possible casing materials are also commonly found, as are casings consisting of different materials within different parts of the surface.

The liquid-permeable casing layer 2 may be constituted by a wholly or partially elastic material so as to give the incontinence protector 1 a better fit during use.

Incontinence protectors 1 comprising absorption bodies 4 which have especially high strength and wear resistance can even work without the need for any extra liquid-permeable casing layer on the side of the incontinence protector 1 which is intended to be facing towards the user during use.

The backing layer 3 also extends beyond the absorption body 4 along the whole of the circumference of the absorption body 4. Normally found backing layers 3 on incontinence protectors 1 are usually impermeable to liquid, but other types of backing layers are also found. The backing layer 3 can consist of a host of different materials. Most commonly, the backing layer 3 is constituted by a thin liquid-impermeable plastic film, but it is also possible to use other types of liquid-impermeable materials, such as nonwoven materials which have been made liquid-impermeable, for example by plastic coating, liquid-impermeable foam layers, liquid-impermeable glue, or the like. The backing layer 3 can also be constituted by a liquid-impermeable, vapour-permeable material. Laminates comprising at least one liquid-impermeable layer arranged against the absorption body 4 are additionally found. Usually, these laminates are constituted by a liquid-impermeable material acting as a liquid barrier and a more textile-like material arranged on the side of the incontinence protector 1 which is orientated away from the user during use, the outer side of the incontinence protector 1 being more clothes-like during use. The textile-resembling layers of the laminate are usually constituted by a nonwoven layer.

The liquid-permeable casing layer 2 and the backing layer 3 are mutually connected outside the absorption body 4 along the whole of its circumference. The layers 2, 3 can be mutually connected in a number of different ways. Examples of connecting methods are gluing, thermobonding, ultrasound welding or the like.

The connected parts of the liquid-permeable casing layer 2 and the backing layer 3 which are arranged outside the longitudinal edges of the absorption body 4 constitute the side flaps 11, 12 of the incontinence protector.

Elastic members 5 are arranged in the side flaps 11, 12, the elastic members 5 raising the side flaps 11, 12 towards the user during use. The raised-up side flaps 11, 12 constitute the side leakage barriers of the incontinence protector 1 and have the task of preventing liquid from leaking out over the longitudinal edges 6, 7 of the incontinence protector 1. The elastic members 5 consist of one or more elastic threads, which, in the stretched state, have been applied between the liquid-permeable casing layer 2 and the backing layer 3, at least in the central parts of the incontinence protector 1 in the longitudinal direction. The elastic members 5 are connected to the backing layer 3 and the casing layer 2 by gluing, ultrasound welding or the like. The elastic members 5 also help the incontinence protector to assume a curved and bowl-shaped configuration.

In alternative embodiments, the elastic members can be arranged on the side of the side flaps 11, 12 which are intended to be facing towards the user during use, or on the opposite side of the side flaps 11, 12, and are in this case, of course, only connected to the casing layer 2 and the backing layer 3 respectively.

The elastic members can be constituted, in alternative embodiments, by elastic ribbon materials made, for example, of foam material.

The absorption body 4 can be made up of one or more layers of cellulose fluff pulp. The cellulose fluff pulp can be mixed with fiber or particles of highly absorbent polymer material, so-called superabsorbent material, of the type which, when absorption occurs, chemically binds large quantities of liquid, forming a liquid-containing gel. The absorption body 4 can also comprise superabsorbent material arranged in a layer inside the absorption body or adjacent to the surface or surfaces of the absorption body. The absorption body 4 can further incorporate additional components for improving the properties of the absorption body 4. Examples of such components are binding fibres, various types of liquid-dispersing layers or fibres, form-stabilizing components, reinforcing fibres or the like. The absorption body 4 can also, of course, consist of other types of absorption materials, such as absorbent nonwoven materials, absorbent foam, textile materials, peat or mixtures of different types of absorption materials.

The absorption body 4 is often created in the production of the incontinence protector 1, the various components of the absorption body 4 being suitably mixed and stratified in the production machine. Absorption bodies produced in separate production lines not connected to the machine producing the incontinence protectors can also be found. Prefabricated absorption material is usually supplied in roll form, the material being cut and folded to prescribed configuration in the machine for producing the incontinence protectors. Prefabricated absorption material can contain the same components as absorption bodies produced directly in the production machine for the incontinence protectors. Binding fibres are, in principle, a necessary component in prefabricated absorption materials to allow them to have sufficient strength to be easily handleable.

Special layers for rapidly absorbing considerable quantities of liquid and temporarily retaining this liquid so as then to deliver the temporarily stored liquid to other parts of the absorption body 4 can also be incorporated in incontinence protectors of the prescribed type. Such absorption layers are in this case normally arranged between the liquid-permeable casing layer 2 of the incontinence protector 1 and the absorption body 4. No absorption layer is shown in FIG. 1.

The incontinence protector 1 is primarily distinguished by the fact that it comprises a material layer 13 disposed on the side of the liquid-permeable casing layer 2 of the incontinence protector 1 which is intended to be facing towards the user during use. The material layer 13 extends from the rear transverse edge 10 of the incontinence protector 1 in the direction of the front transverse edge 9 and has a substantially transverse edge 14 disposed between the front transverse edge 9 and the rear transverse edge 10 of the incontinence protector 1.

The periphery 17 of the material layer 13 is connected to the liquid-permeable casing layer 2 along the longitudinal edges 6, 7 and along the rear transverse edge 10.

The front transverse edge 14 of the material layer 13 is free, which means that it is not connected to the liquid-permeable casing layer 2 of the incontinence protector 1.

The incontinence protector 1 has a pocket 15 between the material layer 13 and the part of the liquid-permeable casing layer 2 which is disposed against the material layer 13, the opening 16 in the pocket being disposed at the transverse edge 14 of the material layer 13. In the use of the incontinence protector 1, the function of the pocket 15 is to enclose the penis, and possibly also the scrotum, of the user and to fasten the incontinence protector 1 to the user in this way.

The material layer 13 is preferably liquid-permeable and substantially non-absorbent.

The liquid-permeable properties of the material layer 13 mean that the user can choose to place the penis inside the pocket 15 or on the side of the material layer 13 which is orientated outwards from the incontinence protector 1 during use of the incontinence protector 1.

If the user chooses the alternative of placing the penis outside the pocket, the material layer 13 has, in principle, no fastening function. In this usage method, the material layer 13 will act only as an extra liquid-permeable casing layer, with no real function. Such use of the incontinence protector 1 requires the incontinence protector 1 to be held in place in an alternative manner. Tight-fitting underpants or the like are the most natural fastening method in this case.

The advantage of choosing a substantially liquid-permeable material for the material layer 13 is, above all, that the user is given options to choose to what extent he wishes to use the pocket 15 for fastening the incontinence protector 1 and in this case to place the penis inside the pocket, or whether he wishes to place the penis outside the pocket and fasten the incontinence protector in an alternative manner. In addition to the pocket 15, the incontinence protector 1 can also, of course, be provided with fastening members on the side which is intended to be facing away from the user during use, which fastening members can be of the adhesive type, of the hook-and-loop type, or the like, and can be intended to be fastened to the underpants of the user.

A further advantage with the choice of a substantially liquid-permeable material for the material layer 13 is that such materials are also normally air-permeable. Owing to the air permeability, the fastening alternative in which the penis is placed inside the pocket 15 will therefore not feel as confined or as sweaty as if a denser material had been chosen.

The material layer 13 is, for example, a non-absorbent SMS material, which has a liquid column exceeding 100 mm when tested with EDANA method 120.2-02.

One example of a suitable material for the material layer 13 is Corovin G15AH05 (15 g/m$^2$), which can be purchased from BBA Fiberweb, Peine, Germany. Other suitable materials are Lutrasil 2020 (20 g/m$^2$), sold by Freudenberg in Germany, or SMPHOB (13 g/m$^2$), marketed by Tesalca in Spain.

The incontinence protector including the backing layer 3, the liquid-permeable casing layer 2 and the absorption body 4, has a certain flexural rigidity, which means that this part endeavours to regain its initial extent when it is bent, the pocket 15 endeavouring to close together gently around the penis during use. Owing to this, the fastening of the incontinence protector 1 around the penis is positively influenced.

In alternative embodiments, the material layer 13 can exhibit elastic properties, at least in the direction transversely to the longitudinal line of symmetry 8 of the incontinence protector 1. The elastic properties can be procured by the material layer being constituted by an elastic nonwoven, or by elastic threads or ribbons having been attached to the material layer. It is also conceivable for the material layer to be constituted by a laminate consisting of an elastic film laminated between two nonwoven layers or the like.

Figure 2:
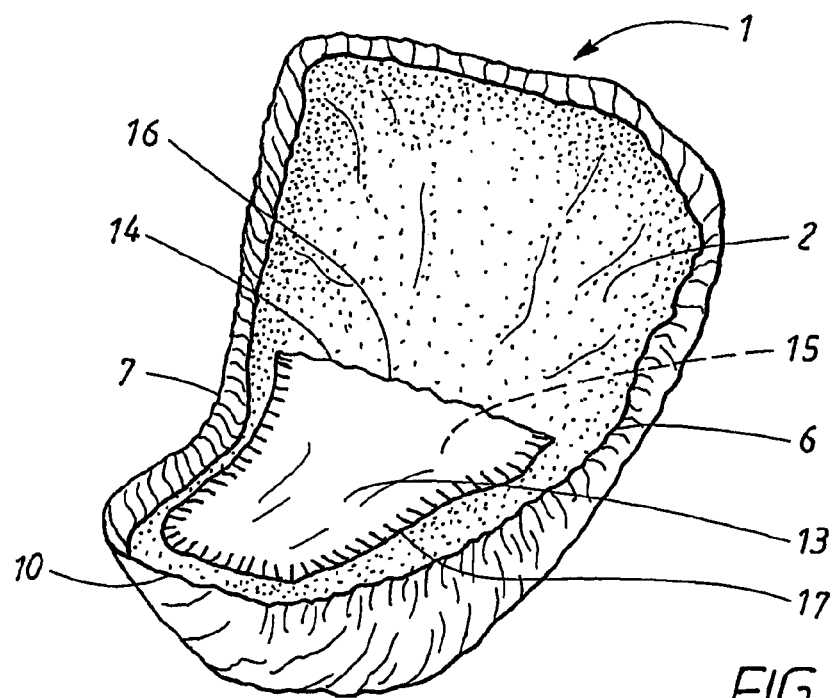
FIG. 2 shows an alternative embodiment of an incontinence protector according to the invention, viewed from the side which, during use, is intended to be facing towards the user.

In FIG. 2, an incontinence protector 1 according to an alternative embodiment is shown. This incontinence protector 1 also comprises an extra material layer 13, a pocket 15 being created between the liquid-permeable casing layer 2 and the material layer 13.

The material layer 13 is connected along its periphery 17 to the liquid-permeable casing layer 2 of the incontinence protector 1 inside the longitudinal edges 6, 7 and rear transverse edge 10 of the incontinence protector 1. The layers 13, 2 can be mutually connected in a number of different ways. Examples of connecting methods are gluing, thermobonding, ultrasound welding or the like.

The material layer 13 has a front transverse edge 14 which is not connected to the liquid-permeable casing layer 2, the opening 16 in the pocket 15 being disposed at the transverse edge 14.

Figure 3:
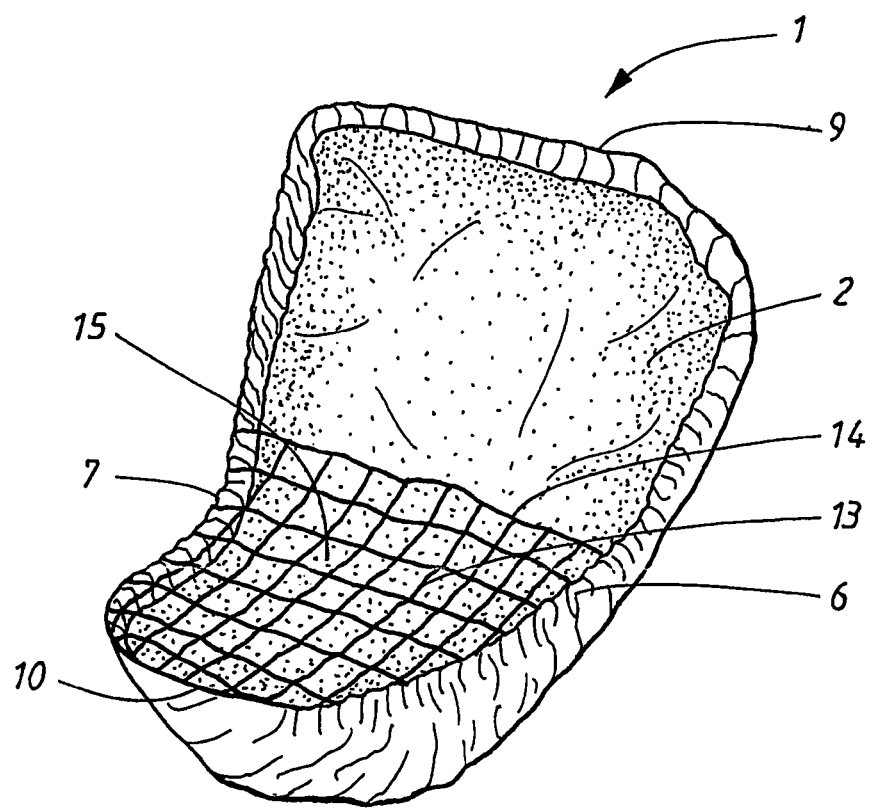
FIG. 3 shows a further alternative embodiment of an incontinence protector according to the invention from the side which, during use, is intended to be facing towards the user.

In FIG. 3, an incontinence protector 1 according to another alternative embodiment is shown.

In this embodiment, the material layer 13 is constituted by an open mesh material. The material layer 13 has the same extent over the liquid-permeable casing layer 2 of the incontinence protector 1 as have corresponding material layers in FIG. 1.

The material layer 13 extends from the rear transverse edge 10 of the incontinence protector 1 in the direction of the front transverse edge 9 and has a substantially transverse edge 14 disposed between the front transverse edge 9 and the rear transverse edge 10 of the incontinence protector 1.

The material layer 13 is connected to the liquid-permeable casing layer 2 along the longitudinal edges 6, 7 and along the rear transverse edge 10.

The transverse edge 14 of the material layer 13 is free, a pocket 15 being formed between the material layer 13 and the liquid-permeable casing layer 2.

Suitable mesh materials for the material layer 13 can be purchased from Conwed Plastic, Minneapolis, Minn. in the USA. An elastic mesh material with the designation T60009 or a non-elastic material with the designation TN4640 can be suitable choices in this regard.

The embodiment exhibits especially good properties with regard to airiness and comfort, of course, when the incontinence protector 1 is fastened by the penis being placed inside the pocket 15.

When the incontinence protector 1 is fastened in an alternative manner, that is to say with the penis placed outside the pocket 15, the liquid-absorbing properties of the incontinence protector 1 are not at all impaired, owing to the openness of the material layer 13.

The invention also embraces all conceivable combinations of the described illustrative embodiments.

Nor is the invention limited to the abovementioned illustrative embodiments, but is naturally applicable to other embodiments within the scope of the following patent claims and equivalents thereof.

The invention claimed is:

1. An incontinence protector for males, comprising a front transverse edge facing forwards during use, a rear transverse edge facing rearwards during use, a length of the front transverse edge being greater than a length of the rear transverse edge, two longitudinal edges, an upper liquid-permeable casing layer, a lower backing layer, an absorption body disposed between the liquid-permeable casing layer and the backing layer, and a substantially non-absorbent material layer disposed on a side of the liquid-permeable casing layer which is oriented away from the absorption body, a periphery of the material layer being connected to at least one of the liquid-permeable casing layer or the backing layer along the rear transverse edge and along or adjacent the two longitudinal edges, wherein the material layer has a front transverse edge, the front transverse edge being free, wherein a pocket is formed between the material layer and the liquid-permeable casing layer and wherein an opening of the pocket is disposed at the front transverse edge of the material layer.

2. The incontinence protector according to claim 1, wherein the substantially non-absorbent material layer is constituted by a mesh.

3. The incontinence protector according to claim 1, wherein the substantially non-absorbent material layer is constituted by a nonwoven.

4. The incontinence protector according to claim 1, wherein the substantially non-absorbent material layer exhibits elastic properties.

5. The incontinence protector according to claim 4, wherein the substantially non-absorbent material layer comprises elastic members.

6. The incontinence protector according to claim 5, wherein the elastic members are constituted by elastic threads or elastic ribbons, the threads or ribbons extending substantially in the transverse direction of the incontinence protector.

7. The incontinence protector according to claim 4, wherein the substantially non-absorbent material layer is constituted by an elastic nonwoven.

8. The incontinence protector of claim 1, wherein the incontinence protector is disposable.

9. The incontinence protector according to claim 2, wherein the substantially non-absorbent material layer exhibits elastic properties.

10. The incontinence protector according to claim 3, wherein the substantially non-absorbent material layer exhibits elastic properties.

11. The incontinence protector according to claim 9, wherein the substantially non-absorbent material layer comprises elastic members.

12. The incontinence protector according to claim 10, wherein the substantially non-absorbent material layer comprises elastic members.

13. The incontinence protector according to claim 11, wherein the elastic members are constituted by elastic threads or elastic ribbons, the threads or ribbons extending substantially in the transverse direction of the incontinence protector.

14. The incontinence protector according to claim 12, wherein the elastic members are constituted by elastic threads or elastic ribbons, the threads or ribbons extending substantially in the transverse direction of the incontinence protector.

15. The incontinence protector according to claim 9, wherein the substantially non-absorbent material layer is constituted by an elastic nonwoven.

16. The incontinence protector according to claim 10, wherein the substantially non-absorbent material layer is constituted by an elastic nonwoven.

17. The incontinence protector according to claim 1, wherein the material layer is connected to the liquid-permeable casing layer inside the two longitudinal edges.

18. The incontinence protector according to claim 1, wherein the material layer is connected to the liquid-permeable casing layer along the two longitudinal edges.

19. The incontinence protector according to claim 1, wherein the opening of the pocket faces the front transverse edge of the incontinence protector.

20. The incontinence protector according to claim 1, wherein the pocket is formed on a portion of the incontinence protector that is closer to the rear transverse edge of the incontinence protector than to the front transverse edge of the incontinence protector.

* * * * *